United States Patent
Kuramochi

(10) Patent No.: US 11,219,561 B2
(45) Date of Patent: Jan. 11, 2022

(54) ABSORBENT ARTICLE

(71) Applicant: DAIO PAPER CORPORATION, Ehime (JP)

(72) Inventor: Mihoko Kuramochi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 379 days.

(21) Appl. No.: 16/317,956

(22) PCT Filed: Jul. 20, 2017

(86) PCT No.: PCT/JP2017/026278
§ 371 (c)(1),
(2) Date: Jan. 15, 2019

(87) PCT Pub. No.: WO2018/021141
PCT Pub. Date: Feb. 1, 2018

(65) Prior Publication Data
US 2019/0290506 A1 Sep. 26, 2019

(30) Foreign Application Priority Data

Jul. 27, 2016 (JP) .............................. JP2016-147873

(51) Int. Cl.
*A61F 13/56* (2006.01)
*A61F 13/472* (2006.01)
(Continued)

(52) U.S. Cl.
CPC ........ *A61F 13/5616* (2013.01); *A61F 13/472* (2013.01); *A61F 13/513* (2013.01);
(Continued)

(58) Field of Classification Search
CPC ............ A61F 13/5616; A61F 13/51456; A61F 13/5611; A61F 13/15203; A61F 13/49; A61F 13/47
(Continued)

(56) References Cited

U.S. PATENT DOCUMENTS

| 4,333,466 | A | * | 6/1982 | Matthews | ........... A61F 13/5611 |
| | | | | | 604/387 |
| 5,330,461 | A | * | 7/1994 | Leeker | ................ A61F 13/5616 |
| | | | | | 604/385.04 |

(Continued)

FOREIGN PATENT DOCUMENTS

| JP | 2011-172658 | 9/2011 |
| JP | 4937225 | 5/2012 |

(Continued)

OTHER PUBLICATIONS

International Search Report for PCT/JP2017/026278 filed on Jul. 20, 2017.
(Continued)

*Primary Examiner* — Tatyana Zalukaeva
*Assistant Examiner* — Nhu Q. Tran
(74) *Attorney, Agent, or Firm* — IPUSA, PLLC

(57) ABSTRACT

An absorbent article includes: a main body (8) including a liquid permeable top sheet (3), a liquid impermeable back sheet (2), and an absorbent body (4) interposed between the top sheet and the back sheet; and a hip-holding portion (H), wherein the main body has a shape having a predetermined length in a front-back direction and a predetermined width in a direction orthogonal to the front-back direction, and wherein the hip-holding portion includes a side region protruding from a side of a rear portion of the main body, the side region including a first projection (41) that includes a portion having a largest width from a center line in the (Continued)

front-back direction of the main body, a first recess (51) that is located adjacent to and forward of the first projection, and a second projection (52) that is located adjacent to and forward of the first recess, and wherein the back sheet in the side region has a slip preventive portion for securing the absorbent article, the slip preventive portion being disposed so as to straddle, in the front-back direction, a virtual line that is drawn in the width direction from a bottom point of the first recess.

4 Claims, 6 Drawing Sheets

(51) Int. Cl.
    *A61F 13/513*     (2006.01)
    *A61F 13/514*     (2006.01)
    *A61F 13/53*     (2006.01)
    *A61F 13/47*     (2006.01)

(52) U.S. Cl.
    CPC ........ *A61F 13/51456* (2013.01); *A61F 13/53* (2013.01); *A61F 2013/4706* (2013.01)

(58) Field of Classification Search
    USPC .......................................................... 604/385
    See application file for complete search history.

(56) References Cited

U.S. PATENT DOCUMENTS

2004/0243087 A1    12/2004    Kinoshita et al.
2010/0312215 A1*  12/2010    Odoi ..................... A61F 13/476
                                                               604/385.04

FOREIGN PATENT DOCUMENTS

| JP | 2014-036832 | 2/2014 |
| --- | --- | --- |
| JP | 2014-144140 | 8/2014 |
| JP | 2014-223216 | 12/2014 |
| JP | 2016-119988 | 7/2016 |

OTHER PUBLICATIONS

Japanese OA dated Aug. 29, 2017 for JP2016-147873.
Extended European search report for European Patent Application No. 17834149.1 dated Jun. 14, 2019.

* cited by examiner

ABSORBENT ARTICLE

TECHNICAL FIELD

The present invention generally relates to an absorbent article.

BACKGROUND ART

Conventionally, as an absorbent article such as a panty liner, a sanitary napkin, and an incontinence pad, an absorbent article that includes an absorbent body interposed between a liquid permeable top sheet and a liquid impermeable back sheet is known.

Further, in recent years, an absorbent article is known that includes an extended portion in which both sides of a rear portion are extended in width and in which a rear end portion is extended in length, so as to prevent body fluids from leaking from the back and/or from the rear right and left sides of the absorbent article.

For example, Patent Document 1 discloses an absorbent article including a hip flap portion. The hip flap portion includes a first constricted portion, a first flap portion that is located rearward of the first constricted portion, projects outward in the width direction relative to the first constricted portion, and has a portion in which the width of the hip flap portion becomes the largest, and a second flap portion that is located forward of the first constricted portion and projects outward in the width direction relative to the first constricted portion. The hip flap portion disclosed in Patent Document 1 also includes a side adhesive portion on a non-skin contact surface. This side adhesive portion is located inward in the width direction relative to an inner edge of the outer compressed grooves of the first flap, and also located inward in the width direction relative to the first constricted portion.

Patent Document 2 discloses a sanitary napkin including rear flaps each projecting sideways and extending from a projection starting point, located rearward of a fold-back flap, to a rear edge. Each of the rear flaps has a shape such that a largest width portion is located forward of a middle point of the length extending from the projection starting point to the rear edge, and the width becomes gradually smaller from the largest width portion towards the rear edge. A pressure-sensitive adhesive layer is provided on a clothing-side surface of each of the rear flaps. The pressure-sensitive adhesive layer is disposed at the largest width portion or 10 mm forward or rearward of the largest width portion.

RELATED-ART DOCUMENTS

Patent Documents

[Patent Document 1] Japanese Unexamined Patent Application Publication No. 2014-36832
[Patent Document 2] Japanese Patent No. 4937225

SUMMARY OF THE INVENTION

Problem to be Solved by the Invention

However, in the absorbent article disclosed in Patent Document 1, the constricted portion of the hip flap portion tends to become wrinkled, causing a gap to be formed between the hip flap portion and a wearer's body. As a result, the fit of the hip flap portion may decrease.

Further, with the shape of the rear flaps of the sanitary napkin disclosed in Patent Document 2, the rear flaps are not flexibly deformed following the roundness of buttocks. Also, although the rear flaps are each provided with the pressure-sensitive adhesive layer, the relationship between the adhesive layer and wrinkles are not taken into account.

In light of the above, it is an object of the present invention to provide an absorbent article that prevents a hip-holding portion from being wrinkled and improves the fit of the hip-holding portion to a wearer's body.

Means to Solve the Problem

In order to solve the above-described problems, according to a first aspect of the present invention, an absorbent article including a main body that includes a liquid permeable top sheet, a liquid impermeable back sheet, and an absorbent body interposed between the top sheet and the back sheet, and that also includes a hip-holding portion is provided. The main body has a shape having a predetermined length in a front-back direction and a predetermined width in a direction orthogonal to the front-back direction, and the hip-holding portion includes a side region protruding from a side of a rear portion of the main body. The side region includes a first projection that includes a portion having a largest width from a center line in the front-back direction of the main body, a first recess that is located adjacent to and forward of the first projection, and a second projection that is located adjacent to and forward of the first recess. The back sheet in the side region has a slip preventive portion for securing the absorbent article. The slip preventive portion is provided so as to straddle, in the front-back direction, a virtual line that is drawn in the width direction from a bottom point of the first recess.

According to the above first aspect, the side region of the hip-holding portion includes a first projection that includes a portion having a largest width from a center line in the front-back direction of the main body, a first recess that is located adjacent to and forward of the first projection, and a second projection that is located adjacent to and forward of the first recess. Therefore, when the absorbent article is worn such that the hip-holding portion is attached along the buttocks, the first projection and the second projection can be deformed independently without affecting each other because the first recess is interposed between the first projection and the second projection. Accordingly, the hip-holding portion can be deformed following the curved surface shape (roundness) of the buttocks, allowing the fit of the hip-holding portion to the wearer's body to be enhanced.

However, when the wearer's body is moved, relatively large pressure may be applied to the outer periphery of the hip-holding portion, depending on the contact state between the hip-holding portion H and the body or depending on the state in which the body weight is applied to the buttocks. In such a case, as stress tends to be concentrated in a recess, wrinkles tend to be formed around the first recess.

In light of the above, the back sheet in the side region is provided with the slip preventive portion for securing the absorbent article, and the slip preventive portion is disposed so as to straddle, in the front-back direction, the virtual line that is drawn in the width direction from the bottom point of the first recess. Accordingly, even if relatively large pressure is applied to the hip-holding portion and stress is concentrated in the first recess, it is possible to prevent wrinkles from being formed because a region around the bottom point of the first recess, where wrinkles tend to start to be formed, is fixed to underwear and stress is dispersed. As a result, no gap is formed between the hip-holding portion and the wearer's body, allowing the fit of the hip-holding portion to the body to be maintained.

According to a second aspect of the present invention, the slip preventive portion extends, in the front-back direction, an equal length on both sides of the virtual line that is drawn in the width direction from the bottom point of the first recess.

In the above second aspect, by providing the slip preventive portion so as to extend, in the front-back direction, an equal length on both sides of the virtual line that is drawn in the width direction from the bottom point of the first recess, the slip preventive portion can be fixed in a well-balanced manner, with the position of the first recess, where wrinkled tends to be most likely formed, being the center. Accordingly, it becomes possible to more securely prevent wrinkles to be formed around the first recess.

According to a third aspect of the present invention, an outer-side outline with respect to the width direction of the slip preventive portion has a shape conforming to an outline of the hip-holding portion.

In the above third aspect, an outer-side outline of the slip preventive portion has a shape conforming to an outline of the hip-holding portion. Accordingly, the slip preventive portion can be disposed in the vicinity of the outline of the hip-holding portion. Thus, it becomes possible to prevent the projecting portion adjacent to the first recess from being curled or twisted, while also maintaining an effect of inhibiting wrinkles from being formed around the first recess where wrinkles tend to be most likely formed.

According to a fourth aspect of the present invention, the slip preventive portion has an elongated shape, and a longitudinal axis of the slip preventive portion is aligned approximately in parallel with a virtual line that passes through the bottom point of the first recess and a top point of the first projection.

In the above fourth aspect, the slip preventive portion is disposed so as to conform to the hip-holding portion that is widened backwards, thereby preventing the first projection or a portion thereof located adjacent to and rearward of the first recess from being curled and bent toward the skin side or the underwear side or from being subjected to small wrinkles and twists (hereinafter sometimes referred to as "curls or twists").

According to a fifth aspect of the present invention, the slip preventive portion is disposed so as to also straddle, in the front-back direction, a virtual line that is drawn in the width direction from the top point of the first projection.

In the above fifth aspect, by disposing the slip preventive portion so as to also straddle, in the front-back direction, a virtual line that is drawn in the width direction from the top point of the first projection, a part of the first projection, which has a largest width and thus tends, to be most likely moved when pressure is applied, and a part of the first recess, which tends to be most likely wrinkled, can be securely fixed to the underwear. As a result, it becomes possible to prevent the hip-holding portion from slipping off a predetermined position of the underwear without appreciably impairing an effect or a function of the first projection to be deformed independently. It is also possible to prevent the first projection from being curled and twisted.

According to a sixth aspect of the present invention, the slip preventive portion is disposed so as to extend between a virtual line that is drawn in the width direction from the top point of the first projection and a virtual line that is drawn in the width direction from a top point of the second projection.

In the sixth aspect, by disposing the slip preventive portion so as to extend between a virtual line that is drawn in the width direction from the top point of the first projection and a virtual line that is drawn in the width direction from a top point of the second projection, it becomes possible to prevent wrinkles from being formed around the first recess that is interposed between the first projection and the second projection, without appreciably impairing an effect or a function of the first projection and the second projection to be deformed independently.

Effects of the Invention

According to one aspect of the present invention, an absorbent article that prevents a hip-holding portion from being wrinkled and improves the fit of the hip-holding portion to a wearer's body is provided.

MODE FOR CARRYING OUT THE INVENTION

In the following, embodiments of the present invention are described with reference to the accompanying drawings.

Figure 1:
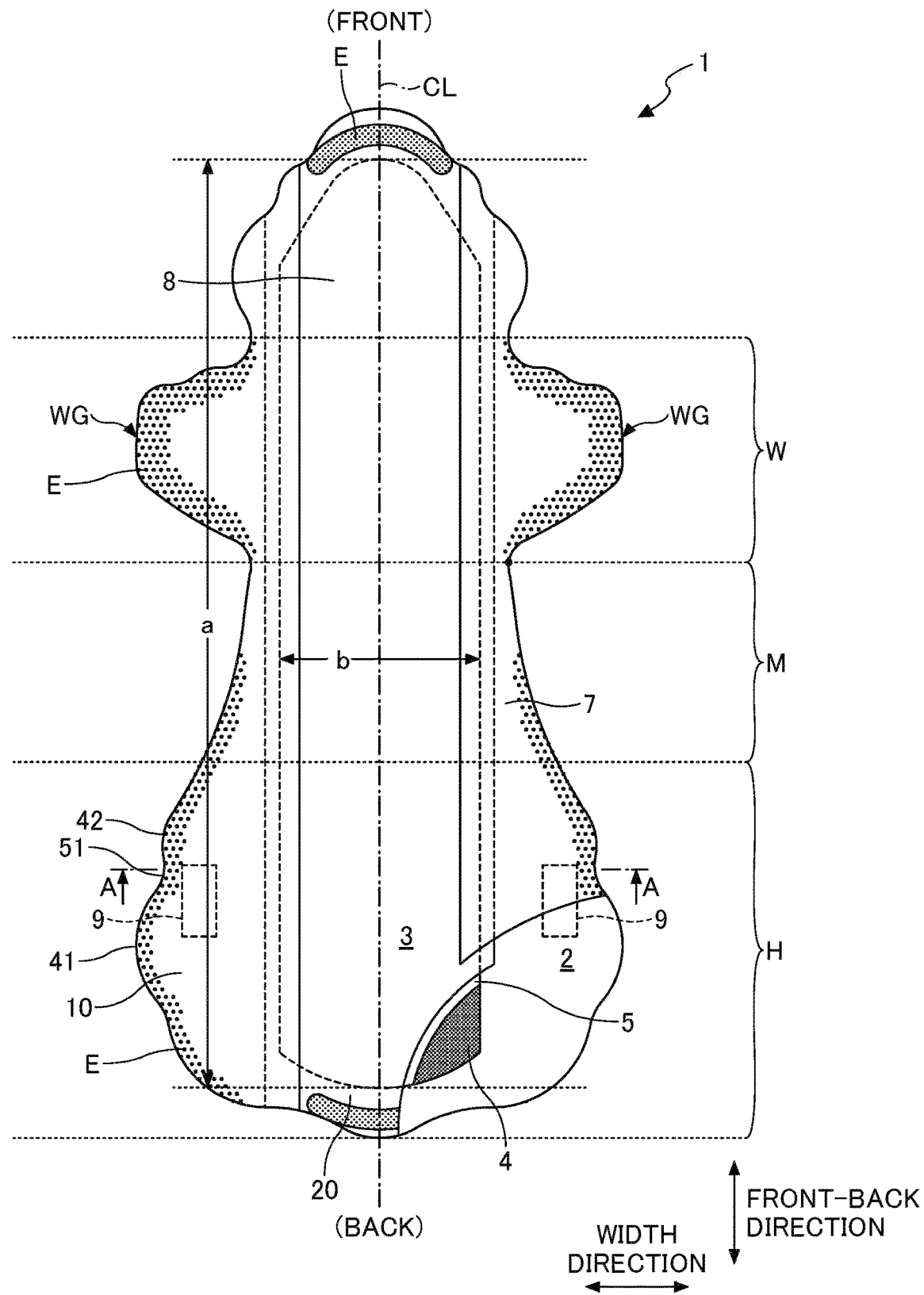
FIG. 1 is a partially expanded view of an absorbent article according to one embodiment.
Figure 2:
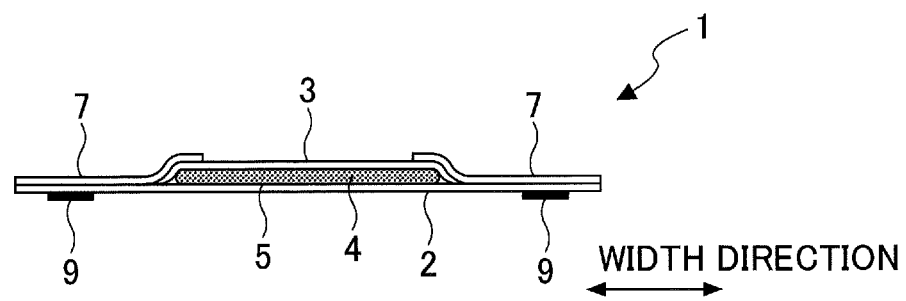
FIG. 2 is a cross sectional view taken along A-A of the absorbent article according to one embodiment.

As illustrated in FIG. 1 and FIG. 2, an absorbent article 1 includes a main body 8 (a main body of the absorbent article). The main body 8 includes a liquid impermeable back sheet 2, a liquid permeable top sheet 3, and an absorbent body 4 interposed between the sheets 2 and 3. In order to maintain the shape of the absorbent body 4, the absorbent body 4 may be surrounded by an encapsulating sheet 5 made of a crepe paper sheet or a non-woven fabric. Further, as illustrated in FIG. 1, the absorbent article 1 includes a hip-holding portion H, which will be described later, and a wing portion having a wing WG on each side. A middle portion M is provided between the hip-holding portion H and the wing portion W. As illustrated in FIG. 1, the middle portion M is a region extending from a rear end of the wing WG to a front end of a second projection 42.

When the absorbent article 1 is worn, the absorbent article 1 is attached to underwear such that the wing portion W faces a front direction and the hip-holding portion H faces a back direction. The main body 8 is formed in an elongated shape having a predetermined length in the front-back direction and also having an approximately uniform width b in a direction orthogonal to the front-back direction. Also, the absorbent article 1 is approximately line symmetrical about a center line CL extending in the front-back direction.

At front and back edge portions of the absorbent body 4, outer edges of the back sheet 2 and the top sheet 3 are bonded to each other with an adhesive such as a hot-melt adhesive or with an adhesive means such as a heat seal or an ultrasonic seal. Furthermore, a side non-woven fabric 7 is provided at each side of the top sheet along the front-back direction (longitudinal direction). The side non-woven fabric 7 partially projects laterally with respect to the main body 8, and is layered onto the back sheet 2 that also projects laterally. The side non-woven fabric 7 and the back sheet 2 are bonded to each other with an adhesive such as a hot-melt adhesive or with an adhesive means such as a heat seal and an ultrasonic seal, thereby forming a side region 10 of the hip-holding portion H and the wing WG.

The back sheet 2 may use a sheet material such as an olefin resin sheet formed of polyethylene or polypropylene and having at least a water shielding property. The back sheet 2 may also use a polyethylene-sheet-laminated non-woven fabric or a non-woven fabric layered sheet having a waterproof film interposed therebetween such that impermeability is substantially ensured. Further, in order to prevent stuffiness, a material having moisture permeability is desirably used. As such a water shielding and permeable sheet material, a microporous sheet is preferably used. The microporous sheet is obtained by forming a sheet by melting and kneading inorganic filler with olefin resin such as polyethylene and polypropylene, and subsequently stretching the sheet in one axial direction or two axial directions.

The top sheet 3 is formed of a liquid permeable sheet that allows menstrual blood, vaginal discharge, and the like to quickly pass through. As the top sheet 3, a perforated or an imperforated non-woven fabric, a porous plastic sheet, or the like is preferably used. Examples of a material fiber forming the non-woven fabric include a synthetic fiber such as an olefin-based synthetic fiber such as polyethylene or polypropylene, a polyester-based synthetic fiber, and a polyamide-based synthetic fiber, a regenerated fiber such as rayon or cuprammonium rayon, and a mixed fiber thereof, and a natural fiber such as cotton. These fibers can be used alone or in combination with two or more kinds. Further, examples of a non-woven fabric processing method include a spunlace method, a spunbond method, a thermal bond method, a melt blown method, and a needle punch method. Among these processing methods, the spunlace method is preferred in terms of flexibility, the spunbond method is preferred in terms of allowing a non-woven fabric with high drape properties to be manufactured, and the thermal bond method is preferred in terms of allowing a soft non-woven fabric with high bulkiness to be manufactured. Further, a composite fiber such as a core-in-sheath fiber having a high-melting-point fiber as a core and a low-melting-point fiber as a sheath, a side-by-side fiber, or a split fiber may be preferably used.

The absorbent body 4 interposed between the back sheet 2 and the top sheet 3 may use any material as long as the material can absorb and retain body fluids. Preferably, the absorbent body 4 includes cotton-like pulp and a water-absorptive polymer. As the water-absorptive polymer, a superabsorbent polymer (SAP), a superabsorbent fiber (SAF), or a combination thereof may be used. Examples of the pulp include chemical pulp made from wood, cellulose fibers such as dissolving pulp, and synthetic cellulose fibers such as rayon and acetate. Materials of the chemical pulp include softwood pulp and hardwood pulp. Because of a long fiber length, the softwood pulp is preferably used.

Further, a synthetic fiber may be mixed into the absorbent body 4. Examples of the synthetic fiber that may be used include polyolefin fibers such as polyethylene and polypropylene, polyester fibers such as polyethylene terephthalate and polybutylene terephthalate, polyamide fibers such as nylon, and a copolymer thereof. Also, a mixture of two types of the above-described fibers may be used. Further, a composite fiber such as a core-in-sheath fiber having a high-melting-point fiber as a core and a low-melting-point fiber as a sheath, a side-by-side fiber, or a split fiber may be used. A hydrophobic fiber may also be used by being subjected to surface treatment with a hydrophilizing agent such that hydrophilicity with body fluids is provided.

The absorbent body 4 preferably has a thickness of approximately 0.5 to 25 mm. The absorbent body 4 does not necessarily have a uniform thickness over the entire surface, and a portion of the absorbent body 4 corresponding to a body fluid discharge region may protrude. Also, the absorbent body is preferably manufactured by a fiber lamination method or an air laid method.

As the side non-woven fabric 7, a water-repellent non-woven fabric or a hydrophilic non-woven fabric may be used. For example, in order to prevent menstrual blood or vaginal discharge from permeating or enhancing texture, a water-repellent non-woven fabric coated with a silicon-based, a paraffin-based, or an alkyl-chromic-chloride-based water-repellent agent is preferably used. Also, in order to enhance absorbency such that menstrual blood is absorbed in the hip-holding portion H, a hydrophilic non-woven fabric is preferably used. As an example type of a non-woven fabric, a soft air-through non-woven fabric is preferably used as it is not readily twisted and wrinkled.

As illustrated in FIG. 1, embossed portions E having dot embossments or embossments of a predetermined pattern may be provided at predetermined positions of the side region 10 and the wing WG of the wing portion W, such that the side non-woven fabric 7 and the back sheet 2 are bonded to each other and the stiffness improves.

In the present embodiment, the absorbent article 1 includes the main body 8 having the liquid permeable top sheet 3, the liquid impermeable back sheet 2, and the absorbent body 4 interposed between the top sheet 3 and the back sheet 2, and includes the hip-holding portion H.

Figure 10:
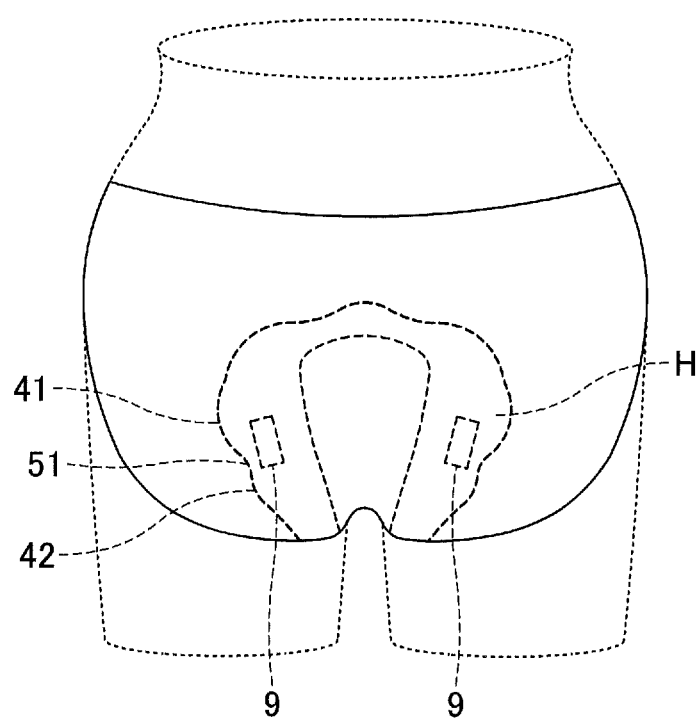
FIG. 10 is a model view illustrating a state in which the absorbent article according to one embodiment is worn.

The hip-holding portion H is an enlarged area in which both sides of a rear portion of the absorbent article are extended in width and also a rear end portion of the absorbent article is extended in length. As illustrated in FIG. 10, when the absorbent article 1 is worn, the hip-holding portion H is attached to the underwear on the buttocks side so as to prevent body fluids from leaking from the back and/or from the rear right and left sides. As illustrated in FIG. 1, the hip-holding portion H includes flap portions where the side non-woven fabric 7 and the back sheet 2 are layered and that protrude from each side of a rear portion of the main body 8 of the absorbent article 1.

The hip-holding portion H includes the side region 10 projecting from a corresponding side of the rear portion of the main body 8, and includes a back region 20 projecting from the rear end of the main body 8. The side region 10 of the hip-holding portion H includes a region in which the back sheet 2 and the side non-woven fabric 7 are mainly bonded to each other. The back region 20 includes a region in which the back sheet 2 and the top sheet 3 are mainly bonded to each other.

The side region 10 and the back region 20 of the hip-holding portion H do not have the absorbent body 4, and are preferably formed thinner than the main body 8. Accordingly, the side region 10 and the back region 20 of the hip-holding portion H can be more flexibly moved than the main body 8. It is also possible to interpose an absorbent body, which is formed thinner than the absorbent body 4 used for the main body 8, between the back sheet 2 and the side non-woven fabric 7 within the hip-holding portion H.

The hip-holding portion H may extend to the rear end of the absorbent article 1, starting from a position that corresponds to a rear end of a crotch portion of the underwear when the absorbent article 1 is worn. In the example of FIG. 1, the hip-holding portion H extends from the front end of the second projection 42 to the rear end of the absorbent article 1. For example, the length of the hip-holding portion H in the front-back direction is preferably greater than or equal to 50 mm and less than or equal to 200 mm, and more preferably greater than or equal to 80 mm and less than or equal to 180 mm. The entire length of the absorbent article 1 can be greater than or equal to 200 mm and less than or equal to 450 mm. The length of the hip-holding portion H in the front-back direction is preferably greater than or equal to 10% and less than or equal to 50% of the entire length of the absorbent article 1. Further, the hip-holding portion H includes a portion where the width of the absorbent article 1 becomes the largest. The largest width is preferably greater than or equal to 120 mm and less than or equal to 230 mm.

Further, the hip-holding portion H has recesses and projections on its outer periphery (outline). For example, as illustrated in FIG. 1, the side region 10 includes a first projection 41 including a portion having a largest width from the center line in the front-back direction of the main body 8, a first recess 51 located adjacent to and forward of the first projection 41, and the second projection 42 located adjacent to and forward of the first recess 51. Also, as illustrated in FIG. 1, the back region 20 extending from the main body may also have recesses and projections.

In the following, an effect obtained by forming recesses and projections on the outer periphery of the hip-holding portion H will be described.

The hip-holding portion H has a flat surface shape as a whole. When the hip-holding portion H having such a flat surface shape is attached to the buttocks, which has a curved surface shape, the outer periphery of the hip-holding portion H may be distorted and wrinkled due to differences between the flat surface shape and the curved surface shape. The sizes and number of wrinkles depend on the entire area of the hip-holding portion H and the shape of the curved surface of the buttocks. However, if the outer periphery of the hip-holding portion H did not have any recess and projection, large wrinkles would be formed at a plurality of locations on the outer periphery of the hip-holding portion H. If such large wrinkles made contact with the skin of the buttocks, discomfort would be applied. In particular, if the wearer was seated on a chair for a long period of time or the wearer was sleeping face up at night, the body weight would be partially applied to the buttocks and thus discomfort or uncomfortableness would increase. Also, if the body weight applied to the buttocks was changed or a contact state between the buttocks and the hip-holding portion H was changed due to a change in a sleeping posture or a seating posture, wrinkles would become larger. Moreover, if the wearer was sleeping face up or on side of body at night, body fluids would readily leak from a gap formed due to such wrinkles.

In light of the above, in the present embodiment, the outer edge of the hip-holding portion H has a recess between two projections. Thus, even if pressure, which may cause a wrinkle, is applied to the first projection 41, the pressure applied to the first projection 41 is not transmitted to the second projection 42 because the first recess 51 is interposed therebetween. Thus, the pressure applied to the first projection 41 remains in an area of the first projection 41. The same applies to a case where pressure, which may cause a wrinkle, is applied to the second projection 42. Accordingly, the first projection 41 and the second projection 42 can be deformed independently without affecting each other. Also, even if a wrinkle is formed, the wrinkle does not become large.

Accordingly, when the absorbent article is worn so as to attach the hip-holding portion H to the buttocks, the hip-holding portion H can be deformed following the curved surface of the buttocks. Thus, the fit of the hip-holding portion H to the buttocks can be enhanced.

In the illustrated example, the first projection 41, the first recess 51, and the second projection 42 are provided in the side region 10 of the hip-holding portion H; however, the number and shapes of recesses and projections are not limited to the illustrated example. For example, two to five projections and one to five recesses may be provided in the side region 10 of the hip-holding portion H.

In the present embodiment, as illustrated in FIG. 1 and FIG. 2, a slip preventive portion 9 for securing the absorbent article 1 is provided on the back sheet 2 of the hip-holding portion H. The slip preventive portion 9 is an adhesive layer or a non-adhesive layer. The hip-holding portion H and underwear are bonded to each other through this layer, thereby preventing the hip-holding portion H from slipping off a predetermined position of the underwear.

As described above, because the recesses and projections are provided on the outer periphery of the hip-holding portion H, the fit of the hip-holding portion H to the wearer's body is improved. However, when legs or buttocks are moved, relatively large pressure may be applied to the outer periphery of the hip-holding portion H, depending on the contact state between the hip-holding portion H and the body or depending on the state in which the body weight is applied to the buttocks. This is because, when legs or buttocks are moved, pressure may be applied from the buttocks to the hip-holding portion H or pressure may be transmitted from the front portion including the middle portion M of the absorbent article 1 to the hip-holding portion H. As a result, there is a possibility that wrinkles may be formed around the first recess 51 where stress tends to be concentrated.

Figure 3:
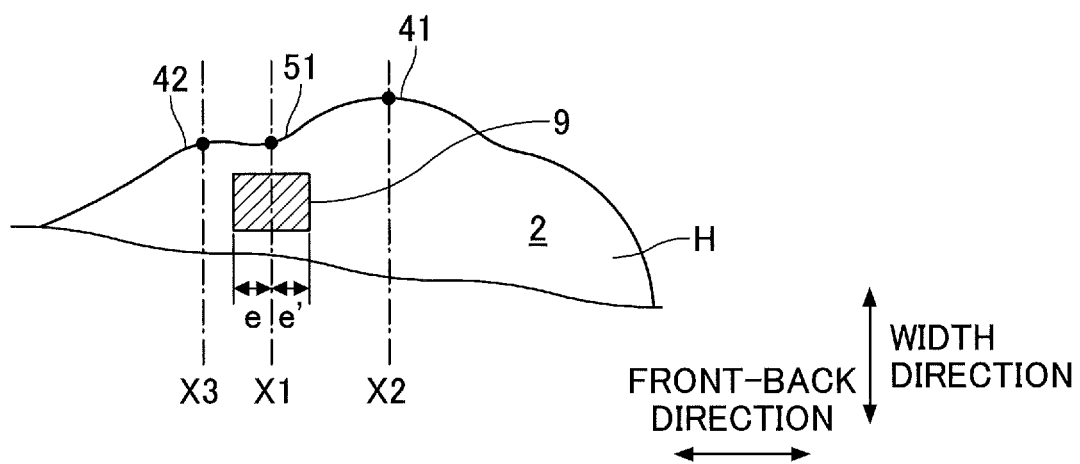
FIG. 3 is a partially enlarged view of a hip-holding portion according to one embodiment when viewed from a back sheet.

In light of the above, in the present embodiment, as illustrated in FIG. 3, the slip preventive portion 9 is disposed so as to straddle, in the front-back direction, a virtual line X1 that is drawn in a width direction from the bottom point of the first recess 51. As a result, an area around the bottom point of the first recess 51 where stress tends to be concentrated can be securely fixed to the underwear. Accordingly, stress concentrated at the bottom point of and around the first recess 51 can be dispersed, thereby preventing wrinkles from being formed.

Also, the above-described improved fit obtained by providing the recesses and projections on the outer periphery of the hip-holding portion H can be maintained. Further, a gap can be prevented from being formed between the hip-holding portion H and the body, thereby preventing body fluids from leaking from the gap. Accordingly, the absorbent article 1 can be used even for a long period of time without any anxiety. Also, discomfort caused when wrinkles of the hip-holding portion H make contact with the buttocks can be eliminated, allowing wearing comfort to improve.

The hip-holding portion H may have a plurality of recesses. In that case, the slip preventive portion 9 may also be provided near a recess other than the first recess 51. In that case, the slip preventive portion 9 is provided so as to straddle, in the front-back direction, a virtual line that is drawn in the width direction from the bottom point of the recess other than the first recess 51. As a result, wrinkles can be prevented from being formed near the recess other than the first recess 51.

Also, the number of slip preventive portions 9 is not limited as long as the virtual line X1 that is drawn in the width direction from the bottom point of the recess is straddled. For example, one to three slip preventive portions 9 may be arranged at predetermined intervals in the width direction. When a plurality of slip preventive portions 9 are provided, the plurality of slip preventive portions 9 may have the same shape and/or size or may have different shapes and/or sizes.

The shape of the slip preventive portion 9 includes, but is not specifically limited to, a triangle shape, a square shape, other polygonal shapes, a circular shape, an elliptical shape, and a diamond shape. In order to disperse stress in the front-back direction, the slip preventive portion 9 preferably has a shape with a predetermined length in the front-back direction, for example, a rectangular shape with the long side in the front-back direction as illustrated in FIG. 3.

The length of the slip preventive portion 9 in the front-back direction is not specifically limited. Preferably, the slip preventive portion 9 has a length that allows the hip-holding portion H to be flexibly deformed, while also allowing the hip-holding portion H to be securely attached to the underwear and maintaining flexibility of the hip-holding portion H in the front-back direction. For example, the length of the slip preventive portion 9 in the front-back direction is preferably greater than or equal to 5 mm and less than or equal to 35 mm, and is more preferably, greater than or equal to 20 mm and less than or equal to 31 mm, although it depends on the shapes and sizes of the first projection 41, the first recess 51, and the second projection 42.

When the slip preventive portion 9 has a rectangular shape, the length of the short side is preferably greater than or equal to 5 mm in order to improve fixing strength to the underwear, and is less than or equal to 20 mm in order to allow the hip-holding portion H to fit the body while also maintaining flexibility of the hip-holding portion H in the width direction so as to be flexibly deformed. The length of the short side is more preferably greater than or equal to 7 mm and is less than or equal to 17 mm.

Further, the slip preventive portion 9 is preferably positioned inwardly away from the bottom point of the first recess 51 in the width direction, although it depends on the shapes and sizes of the first recess 51, the first projection 41, and the second projection 42, and also depends on the shape and the length in the front-back direction of the slip preventive portion 9. Accordingly, it becomes possible to ensure the fit of the hip-holding portion H without hindering the first projection 41 and the second projection 42 located on each side of the first recess 51 from being independently moved. More preferably, the slip preventive portion 9 is positioned greater than or equal to 4 mm and less than or equal to 10 mm inwardly away from the bottom point of the first recess 51 in the width direction.

In a case where the embossed portions E as illustrated in FIG. 1 are provided on the outer edge of the hip-holding portion H, the slip preventive portion 9 is preferably provided inward relative to the embossed portions E such that the back sheet 2 and the slip preventive portion 9 are securely bonded to each other.

As described above, the slip preventive portion 9 can be formed as an adhesive layer or a non-adhesive layer. An adhesive layer mainly containing a styrene-based polymer, a tackifier, a plasticizer, and a combination thereof is preferably used, for example. Examples of the styrene-based polymer include a styrene-ethylene-butylene-styrene block copolymer, a styrene-butylene-styrene block copolymer, a styrene-isoprene-styrene copolymer, and a styrene-butadiene-styrene block copolymer, and one kind or two or more kinds thereof may be used. Among them, the styrene-butadiene-styrene block copolymer is preferred in terms of favorable thermostability.

Also, a tackifier and a plasticizer that are solid at normal temperature can be used. Examples of the tackifier include C5-based petroleum resin, C9-based petroleum resin, dicyclopentadiene-based petroleum resin, rosin-based petroleum resin, polyterpene resin, and terpene phenolic resin. Examples of the plasticizer include monomeric plasticizers such as tricresyl phosphate, dibutyl phthalate, and dioctyl phthalate, and also include polymeric plasticizers such as vinyl polymer and polyester.

As a material of the slip preventive portion 9 formed as a non-adhesive layer, a material such as natural rubber, styrene-butadiene rubber, silicone rubber, chloroprene rubber, isobutylene-isoprene rubber, and styrene-isoprene rubber may be used alone or in combination as a base polymer. Among them, the silicone rubber or a hydrogenated styrene-isoprene-styrene (SIS) or styrene-butadiene-styrene (SBS) elastomer is preferred.

A method for securing the slip preventive portion 9 to the back sheet 2 is not particularly limited; however, hot-melt coating using a hot-melt coater, for example, a hot-melt adhesive is preferred.

Figure 4:
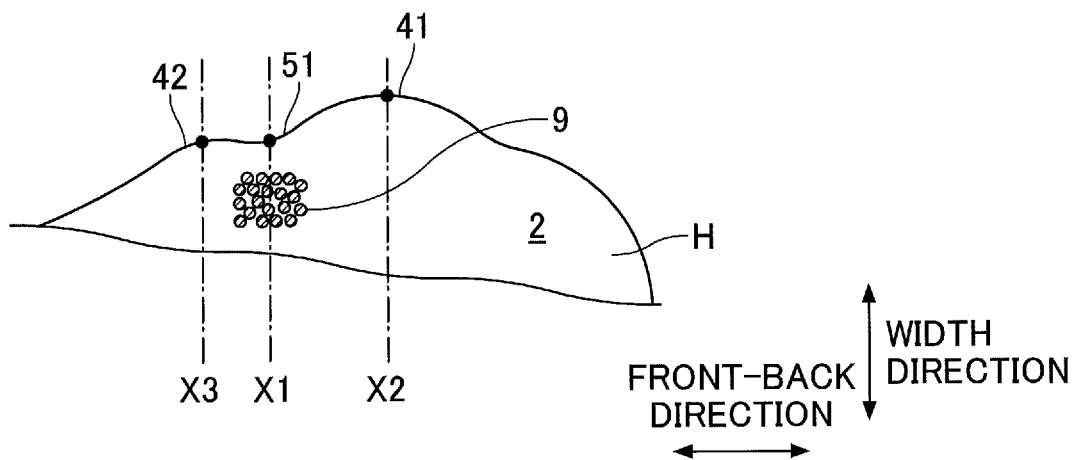
FIG. 4 is a partially enlarged view of the hip-holding portion according to one embodiment when viewed from the back sheet.

When the slip preventive portion 9 is used as a non-adhesive layer, it is preferable to form the slip preventive portion in a dotted pattern, as illustrated in FIG. 4. When the back sheet 2 of the absorbent article is formed of a moisture permeable material, the dotted pattern can minimize inhibition of moisture permeability.

Also, as the non-adhesive slip preventive portion 9, a mechanical fastener hook may be used. The shape of the hook is not specifically limited as long as the hook can be attached to the underwear. Various types of known shapes such as a hook shape and a mushroom shape may be used.

In a state in which the absorbent article 1 is packaged, the slip preventive portion 9 is covered by a separating material that can protect the slip preventive portion 9 and that can also be readily separated from and expose the slip preventive portion when the absorbent article 1 is used. As such a separating material, paper or a plastic sheet subjected to a release treatment by coating or spraying a release agent such as silicone-based resin, fluorine-based resin, or tetrafluoroethylene-based resin may be used.

As illustrated in FIG. 3, the slip preventive portion 9 preferably extends an equal length (distance) e, e' on both sides of the virtual line X1 that is drawn in the width direction from the bottom point of the first recess 51. Accordingly, the first recess 51 can be fixed from both the first projection 41 and the second projection 42 in a well-balanced manner, with the position corresponding to the bottom point of the first recess 51, where wrinkles tend to be most likely formed, being the center. Accordingly, stress around the first recess can be favorably dispersed and wrinkles can be more securely prevented from being formed.

Figure 5:
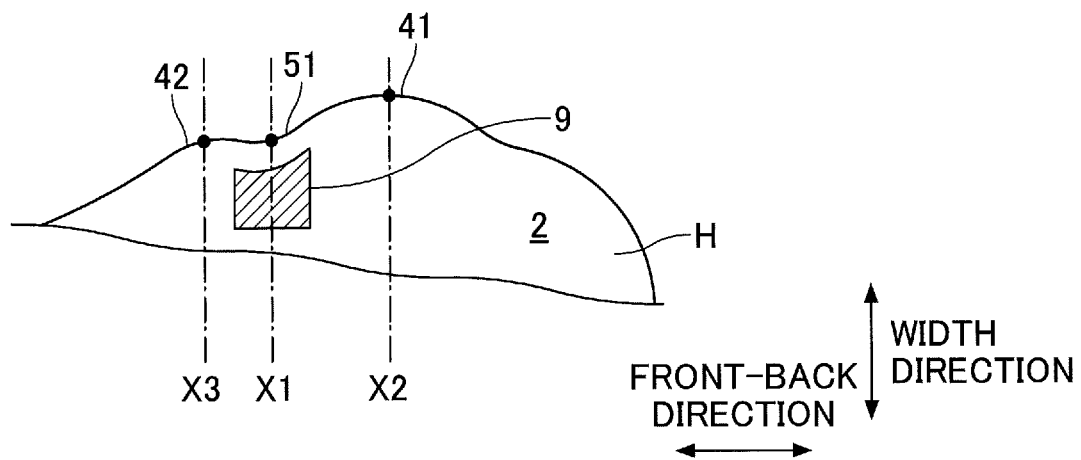
FIG. 5 is a partially enlarged view of the hip-holding portion according to one embodiment when viewed from the back sheet.

Also, the outline of the slip preventive portion 9 may have a curve. For example, as illustrated in FIG. 5, an outer-side outline with respect to the width direction of the slip preventive portion 9 may have a shape conforming to an outline of the hip-holding portion H. In this way, the slip preventive portion 9 can be provided near the outline of the hip-holding portion H, thereby favorably preventing the projections located adjacent to the first recess 51 from being curled and twisted, while also maintaining an effect of inhibiting the bottom point of the first recess 51, where wrinkles tend to be most likely formed, from being wrinkled.

Figure 6:
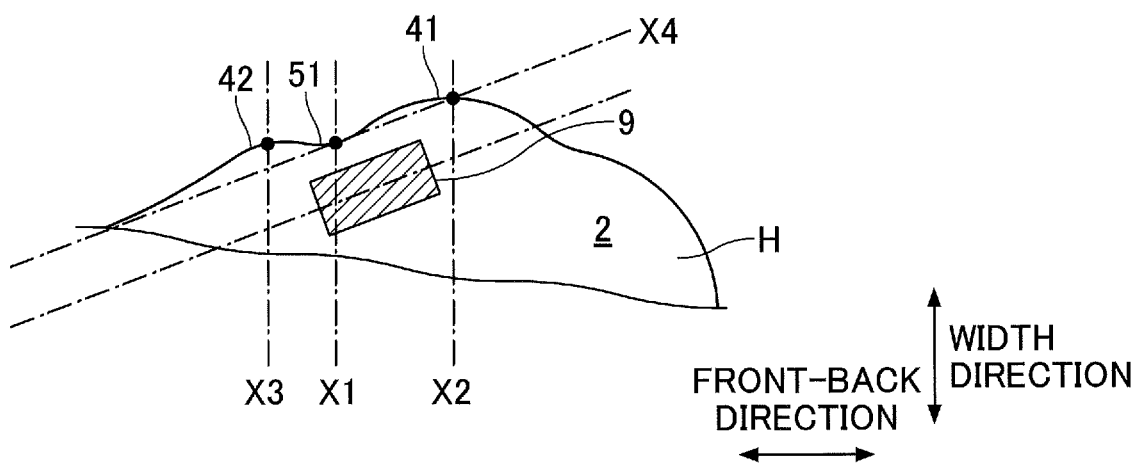
FIG. 6 is a partially enlarged view of the hip-holding portion according to one embodiment when viewed from the back sheet.

As described above, the slip preventive portion 9 preferably has an elongated shape such as a rectangular shape. In such a case, as illustrated in FIG. 6, a longitudinal axis of the slip preventive portion 9 is aligned approximately in parallel with a virtual line X4 that passes through the bottom point of the first recess 51 and a top point of the first projection 41, such that the slip preventive portion can be disposed so as to sufficiently conform to the hip-holding portion H that is widened backwards.

Namely, as illustrated in FIG. 1, even if the first projection 41 is formed into a shape that largely projects outward, the slip preventive portion can be disposed so as to sufficiently conform to the curved shape of the first projection 41. The first projection 41 includes the portion where the width of the hip-holding portion H becomes the largest, and thus tends to be curled or twisted when pressure is applied. However, by disposing the slip preventive portion 9 at an inclined angle relative to the center line in the longitudinal direction, the first projection 41 can be favorably prevented from being curled.

Figure 7:
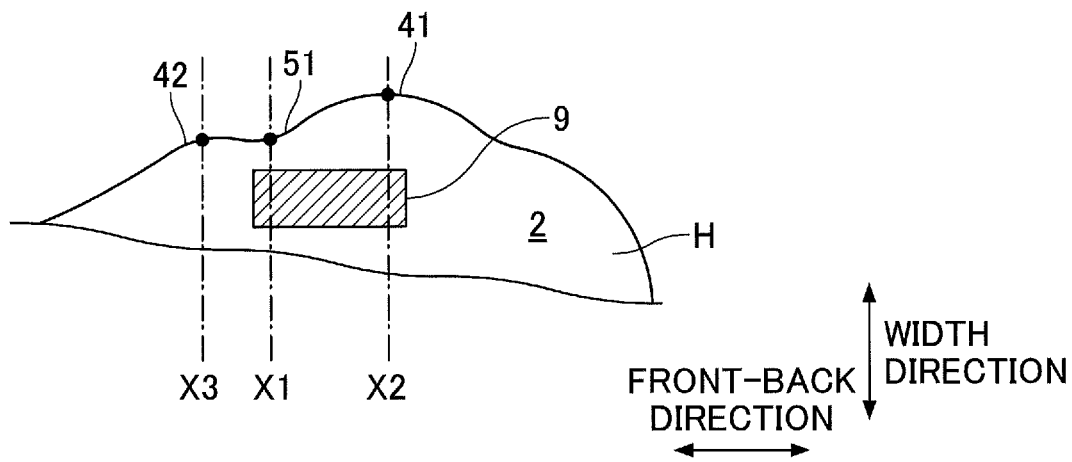
FIG. 7 is a partially enlarged view of the hip-holding portion according to one embodiment when viewed from the back sheet.

As illustrated in FIG. 7, the slip preventive portion 9 may be disposed so as to also straddle a virtual line X2 that is drawn in the width direction from the top point of the first projection 41. Accordingly, the first projection 41, which has the large width and thus tends to be most readily moved when pressure is applied, can be securely attached to the underwear. This prevents the hip-holding portion H from being slipped off the predetermined position of the underwear. It is also possible to prevent the outer edge of the first projection 41 from being curled or twisted.

However, if the slip preventive portion 9 extends far beyond, towards the back, the virtual line X2 drawn in the width direction from the top point of the first projection 41, flexibility in the vicinity of the first projection 41 may be lost, and as a result, the hip-holding portion H may be prevented from being flexibly deformed following the curved surface of the buttocks. Thus, in order for the entire hip-holding portion H to match the shape of the buttocks, the slip preventive portion 9 is preferably disposed so as not to extend 10 mm beyond the virtual line X2, and is more preferably disposed so as not to extend 5 mm beyond the virtual line X2.

Figure 8:
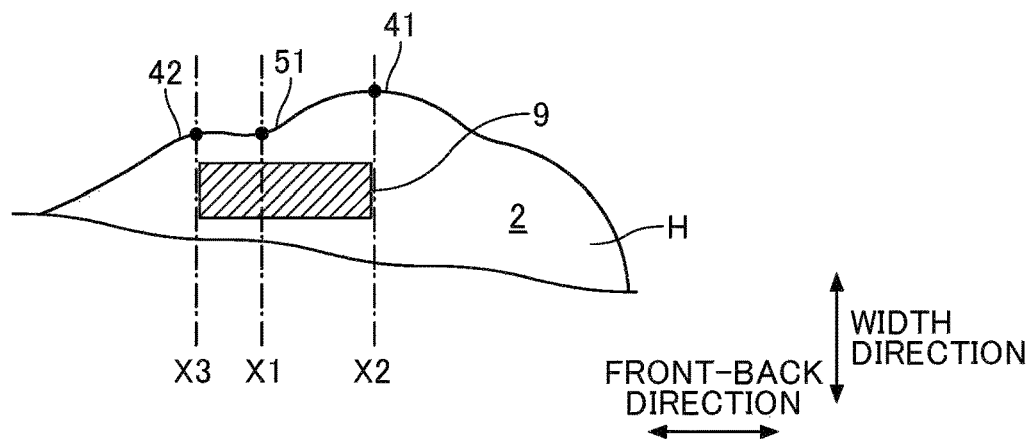
FIG. 8 is a partially enlarged view of the hip-holding portion according to one embodiment when viewed from the back sheet.

Also, as illustrated in FIG. 8, the slip preventive portion 9 may be disposed so as to extend between the virtual line X2 drawn in the width direction from the top point of the first projection 41 and a virtual line X3 drawn in the width direction from the top point of the second projection 42.

Accordingly, the slip preventive portion 9 can have a predetermined length in the front-back direction with respect to the first recess 51, allowing the hip-holding portion H to be securely attached to the underwear. Also, the slip preventive portion 9 can be provided so as not to extend beyond the virtual line X2 that is drawn from the top point of the first projection 41 and not to extend beyond the virtual line X3 that is drawn from the top point of the second projection 42, allowing the first recess 51 to be fixed from both sides. Accordingly, it is possible to favorably disperse stress generated around the first recess 51 and more securely prevent wrinkles from being formed, without appreciably impairing an effect or a function of the first projection 41 and the second projection 42 to be deformed independently.

Figure 9:
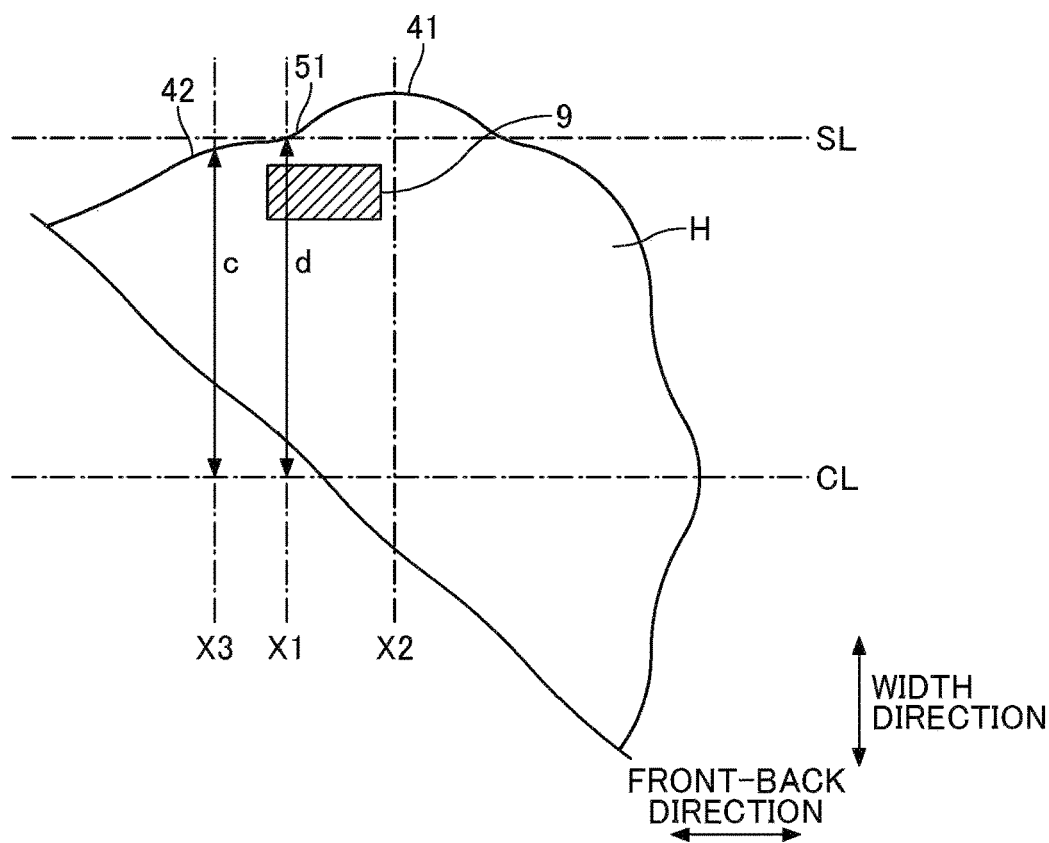
FIG. 9 is a partially enlarged view of the hip-holding portion according to one embodiment when viewed from the back sheet.

As illustrated in FIG. 9, the outline of the side region 10 of the hip-holding portion H may be formed such that a width c of the second projection 42 from the center line CL becomes the same as or smaller than a smallest width d of the first recess 51 from the center line CL. Namely, in a case where a reference line SL that passes through a point where the width of the first recess 51 from the center line CL becomes the smallest (a point connecting the outline of the first recess 51 to the outline of the second projection 42) is drawn in parallel with the center line CL in the front-back direction, the second projection 42 does not protrude outward from the reference line SL.

Accordingly, it becomes possible to inhibit the tendency to cause curls and twists to be generated at the second projection 42, which is positioned closer to the intergluteal cleft when the absorbent article is worn and thus tends to be affected by leg pressure. Thus, the above-described effect or function of the first projection 41 and the second projection 42 being deformed independently can be maintained. Accordingly, it is possible to maintain the fit of the hip-holding portion H to the body while also reducing discomfort caused when a twisted part is brought into contact with the body, thereby improving wearing comfort.

Also, the second projection 42 is further prevented from being curled or twisted because the slip preventive portion 9 disposed so as to straddle the virtual line X1 that is drawn in the width direction from the bottom point of the first recess further approaches the top point of the second projection 42.

The present application is based on and claims priority to Japanese patent application No. 2016-147873 filed on Jul. 27, 2016, with the Japanese Patent Office, the entire contents of which are hereby incorporated by reference.

DESCRIPTION OF THE REFERENCE NUMERAL 1 absorbent article
2 back sheet
3 top sheet
4 absorbent body
5 encapsulating sheet
7 side non-woven fabric
8 main body (main body of absorbent article)
9 slip preventive portion
10 side region
20 back region
41 first projection
42 second projection
51 first recess
H hip-holding portion
W wing portion W
E embossed portions
WG wing
CL center line in front-back direction
SL reference line
X1 virtual line that is drawn in width direction from bottom point of first recess X2 virtual line that is drawn in width direction from top point of first projection
X3 virtual line that is drawn in width direction from top point of second projection
X4 virtual line that passes through bottom point of first recess and top point of first projection

The invention claimed is:

1. An absorbent article comprising
a main body including a liquid permeable top sheet, a liquid impermeable back sheet, and an absorbent body interposed between the top sheet and the back sheet; and a hip-holding portion,
wherein the main body has a shape having a predetermined length in a front-back direction and a predetermined width in a direction orthogonal to the front-back direction, and
wherein the hip-holding portion includes a side region protruding from a side of a rear portion of the main body, the side region including a first projection that includes a portion having a largest width from a center line in the front-back direction of the main body, a first recess that is located adjacent to and forward of the first projection, and a second projection that is located adjacent to and forward of the first recess,
wherein the back sheet in the side region has a slip preventive portion for securing the absorbent article, the slip preventive portion being provided so as to straddle, in the front-back direction, a first virtual line that is drawn in the width direction from a bottommost point of the first recess and a second virtual line that is drawn in the width direction from a topmost point of the first projection.

2. The absorbent article according to claim 1, wherein the slip preventive portion extends, in the front-back direction, an equal length on both sides of the virtual line that is drawn in the width direction from the bottom point of the first recess.

3. The absorbent article according to claim 1, wherein each of the side regions has a single slip preventive portion of the slip preventive portions.

4. An absorbent article comprising:
a main body including a liquid permeable top sheet, a liquid impermeable back sheet, and an absorbent body interposed between the top sheet and the back sheet; and a hip-holding portion,
wherein the main body has a shape having a predetermined length in a front-back direction and a predetermined width in a direction orthogonal to the front-back direction,
wherein the hip-holding portion includes a side region protruding from a side of a rear portion of the main body, the side region including a first projection that includes a portion having a largest width from a center line in the front-back direction of the main body, a first recess that is located adjacent to and forward of the first projection, and a second projection that is located adjacent to and forward of the first recess,
wherein the back sheet in the side region has a slip preventive portion for securing the absorbent article, the slip preventive portion being provided so as to straddle, in the front-back direction, a virtual line that is drawn in the width direction from a bottom point of the first recess, and
wherein the slip preventive portion has an elongated shape, and a longitudinal axis of the slip preventive portion is aligned approximately in parallel with a virtual line that passes through the bottom point of the first recess and a top point of the first projection, and not along the front-back direction.

* * * * *